United States Patent [19]

Hoffman, Jr. et al.

[11] Patent Number: 4,842,575
[45] Date of Patent: Jun. 27, 1989

[54] METHOD FOR FORMING IMPREGNATED SYNTHETIC VASCULAR GRAFTS

[75] Inventors: Harmon Hoffman, Jr., Wyckoff, N.J.; Kemal Schankereli, Stillwater, Minn.

[73] Assignee: Meadox Medicals, Inc., Oakland, N.J.

[21] Appl. No.: 228,613

[22] Filed: Aug. 5, 1988

Related U.S. Application Data

[60] Division of Ser. No. 67,390, Jun. 24, 1987, which is a continuation of Ser. No. 4,765, Jan. 7, 1987, abandoned, which is a continuation of Ser. No. 575,082, Jan. 30, 1984, abandoned.

[51] Int. Cl.$^4$ ............................ A61F 2/06; A61F 2/04
[52] U.S. Cl. ........................................ 600/36; 623/1; 128/DIG. 8; 427/2; 106/124; 514/801
[58] Field of Search ............ 623/1, 66; 426/657; 427/2; 128/DIG. 8; 527/200, 201; 600/36; 106/124, 125; 424/95; 514/801

[56] References Cited

U.S. PATENT DOCUMENTS

| | | | |
|---|---|---|---|
| 3,272,204 | 9/1966 | Artandi et al. | 3/1 |
| 3,425,418 | 2/1969 | Chvapil et al. | 623/1 |
| 3,479,670 | 11/1969 | Medell. | |
| 3,928,653 | 12/1975 | Dowell, Jr. et al. | 426/657 |
| 4,416,028 | 11/1983 | Eriksson et al. | 623/1 |

FOREIGN PATENT DOCUMENTS

| | | |
|---|---|---|
| 0000949 | 3/1979 | European Pat. Off. . |
| 2601289 | 7/1977 | Fed. Rep. of Germany . |
| 0904693 | 2/1982 | U.S.S.R. . |

Primary Examiner—Richard J. Apley
Assistant Examiner—Alan W. Cannon
Attorney, Agent, or Firm—Blum Kaplan

[57] ABSTRACT

A collagen impregnated synthetic vascular graft including a synthetic vascular graft substrate and cross-linked collagen fibril is formed by depositing an aqueous slurry of collagen fibrils in the lumen of the graft and massaging to insure intimate mixing of the fibrils into the porous structure of the substrate. After massaging, the collagen is dried and cross-linked. Repeated applications and massaging and drying further reduce porosity of the graft.

15 Claims, 2 Drawing Sheets

METHOD FOR FORMING IMPREGNATED SYNTHETIC VASCULAR GRAFTS

This is a division of pending application Ser. No. 067,390 filed June 24, 1987, which is a continuation of application Ser. No. 004,765 filed Jan. 7, 1987 and now abandoned, which in turn is a continuation of application Ser. No. 575,082, filed Jan. 30, 1984 and now abandoned.

BACKGROUND OF THE INVENTION

This invention relates to a synthetic vascular graft, and more particularly to a synthetic vascular graft having a series of plasticized collagen fibril applications which renders the graft blood-tight without the need to be preclotted.

The replacement of segments of human blood vessels with synthetic vascular grafts is well accepted in the art. Synthetic vascular grafts have taken a wide variety of configurations and are formed of a wide variety of materials. Among the accepted and successful vascular graft implants are those which ar formed from a biologically compatible material which retains an open lumen to permit blood to flow through the synthetic graft after implant. The grafts may be made from biologically compatible fibers, such as Dacron and Teflon, may be knitted or woven and may be of a monofiliment yarn, multi-filiment yarn or staple yarn.

An important factor in the selection of a particular graft substrate is the porosity of the fabric wall of which the graft is formed. Porosity is significant because it controls the tendency to hemorrhage during and after implantation and controls the ingrowth of tissue into the wall of the graft. It is desirable that the vascular graft substrate be sufficiently blood-tight to prevent the loss of blood during implant, yet the structure must be sufficiently porous to permit ingrowth of fibroblast and smooth muscle cells in order to attach the graft to the host tissue. Synthetic vascular grafts of the type described in U.S. Pats. Nos. 3,805,301 and 4,047,252, assigned to the assignee of the subject application are elongated flexible tubular bodies formed of a yarn such as Dacron. In the earlier patent, the graft is a warp knitted tube and in the latter issued patent it is a double-velour synthetic graft marketed under the trademark Microvel. These types of grafts have sufficiently porous structures to permit ingrowth of host tissue. The general procedure for implantation includes the step of preclotting, wherein the graft is immersed in the blood of the patient and allowed to stand for a period of time sufficient for clotting to insue. After pre-clotting, hemorrhaging does not occur when the graft is implanted and growth of tissue is not impeded. However, it is desirable to avoid pre-clotting as it takes valuable time during surgery.

Blood-tight absorbable collagen reinforced grafts have been proposed in U.S. Pat. No. 3,272,204. The type of collagen disclosed is obtained from the deep flexor tendon of cattle. Tendon-derived collagen is generally highly cross-linked and difficult to process by the enzyme digestion procedure described in the patent. An additional reinforced vascular prosthesis is described in U.S. Pat. No. 3,479,670 which discloses an open mesh cylindrical tube wrapped by an outer helical wrapping of fused polypropylene mono-filiment which may be filled with collagen fibrils to render the prosthesis impermeable to bacteria and fluids. The collagen fibrils utilized are the same as described in U.S. Pat. No. 3,272,204.

The synthetic vascular grafts suggested by the prior art are claimed to be suitable for many applications. However, it remains desirable to provide a flexible vascular graft which exhibits virtually zero porosity, yet remains sufficiently receptive to ingrowth of host tissue and which may be more easily processed than the teachings of the prior art.

SUMMARY OF THE INVENTION

A collagen impregnated synthetic vascular graft formed from a tubular porous structure of a biocompatible filimentary material with cross-linked collagen fibrils admixed with a plasticizer which renders the graft blood-tight without preclotting. The porous graft substrate may be a tubular vascular graft formed of a Dacron material and may be woven or knit.

The collagen source is preferably from bovine skin which has been processed by an acid digestion to result in a fibril dispersion of high purity. An aqueous purified slurry of collagen fibrils including a plasticizer is applied to the synthetic vascular graft by massage to cover the entire surface area to provide a flexible graft with good hand. After at least three repeated applications of collagen and drying applications the collagen is cross-linked by exposure to formaldehyde vapor. Graft porosity is reduced to less than about 1% of the porosity of graft before coating.

Accordingly, it is an object of the invention to provide an improved synthetic vascular graft.

Another object of the invention is to provide an improved blood-tight synthetic vascular graft.

A further object of the invention is to provide an improved collagen-impregnated synthetic vascular graft.

It is another object of the invention to provide an improved bovine skin derived collagen slurry.

It is a further object of the invention to provide an improved method for the preparation of a collagen-impregnated synthetic vascular graft.

Still another object of the invention is to provide an improved process for preparing a synthetic vascular graft with collagen to render the graft blood-tight.

Still other objects and advantages of the invention will in part be obvious and will in part be apparent from the specification.

The invention accordingly comprises the article possessing the features, properties and the relation of elements and the several steps and the relation of one or more of such steps with respect to each of the others, which are exemplified in the following detailed disclosure, and the scope of the invention will be indicated in the claims.

BRIEF DESCRIPTION OF THE DRAWING

For a fuller understanding of the invention, reference is had to the following description taken in connection with the accompanying drawing, in which.

DESCRIPTION OF THE PREFERRED EMBODIMENTS

Figure 1:
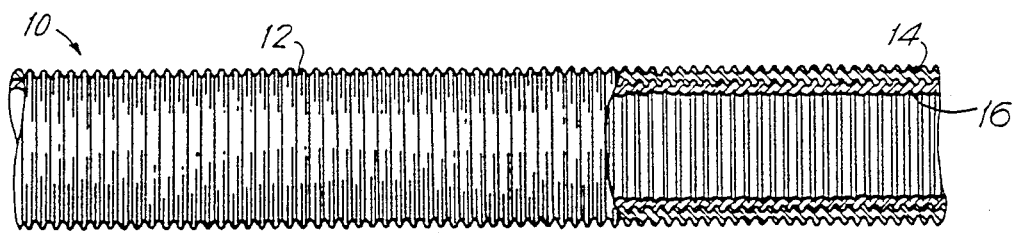
FIG. 1 is a partial cross-sectional view of a collagen-impregnated synthetic vascular graft in accordance with the invention.

A synthetic vascular graft 10 constructed and arranged in accordance with the invention is shown in FIG. 1. Graft 10 includes a tubular substrate portion 12 which is formed of a biologically compatable filamentary synthetic material, preferably a polyethylene terephthalate, such as Dacron. Substrate 12 is a porous Dacron warp knit fabric having an inner and outer velour surface of the type described in U.S. Pat. No. 4,047,252. While tubular portion 12 is formed of Dacron, any biocompatible filimentary material may be used for the substrate provided it may be fabricated into a porous structure which will permit tissue ingrowth and maintain an open lumen for flow of blood.

Figure 2:
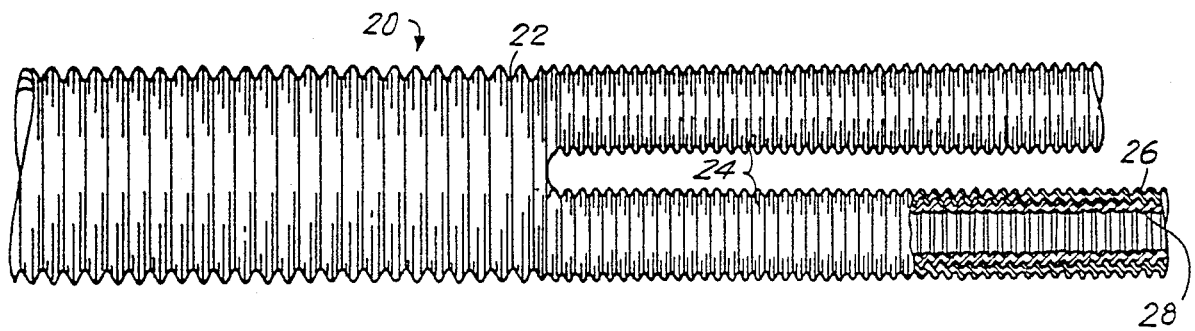
FIG. 2 is a partial cross-sectional view of a branched tubular graft of the type illustrated in FIG. 1.

Tubular portion 12 has on the inner surface a coating of collagen shown as 16. Collagen coating 16 is formed from at least three applications of an aqueous collagen fibril and plasticizer dispersion which has been cross-linked by exposure to formaldehyde vapor. FIG. 2 shows a bifurcated collagen-impregnated graft 20. Graft 20 includes a main tubular portion 22 and two branches 24. Main tubular portion 22 and bifurcated portions 24 are formed from a Dacron knit substrate 26 having an inner surface coating of a collagen coating 28 formed from at least three applications of collagen fibrils.

Porous vascular graft substrates suitable for use in accordance the invention, preferably are produced from Dacron multi-filiment yarns by knitting or weaving processes which are commonly used in manufacture of these products. Generally, the porosity of the Dacron substrate ranges from about 2,000 to 3,000 ml/min-cm$^2$ (purified water at 120 mm Hg). The cross-linked collagen is applied by filling a tubular substrate with a collagen and plasticizer slurry and massaging manually, removing the excess and permitting the deposited dispersion to dry. After the final application, the collagen is cross-linked by exposure to formaldehyde vapor, air dried and then vacuum dried to remove excess moisture and excess formaldehyde. The collagen grafts in accordance with the invention have essentially zero porosity.

The following examples are set forth to illustrate the method of preparing purified collagen from bovine skin and grafts in accorance with the invention. The examples are set forth for purposes of illustration and not intended in a limiting sense.

EXAMPLE 1

Fresh calf skins were mechanically stripped from young calves, fetuses or stillborns and washed in a rotating vessel with cold running water until the water was observed to be free from surface dirt, blood and/or tissues. The subcutis was mechanically cleaned to remove contaminating tissues, such as fat and blood vessels. Subsequently, the skins were cut in the longitudinal direction into strips about 12 cm wide and were placed in a wood or plastic vessel as commonly used in the leather industry.

The skins were dehaired by using a flusher solution of 1M Ca(OH)$_2$ for 25 hours. Alternatively, the skin may be dehaired by mechanical means or by a combination of chemical and mechanical means. Following the dehairing, the skins were cut into small size pieces about 1"×1" and were washed in cold water.

Following washing, 120 Kg of the bovine skin was placed in a vessel having 260 L water, 2 L NaOH (50%) and 0.4 L H$_2$O$_2$ (35%). The components were mixed slowly for 12 to 15 hours at 4° C. and washed with an excess of tap water for 30 minutes to provide partially purified skins. The partially purified skins were treated in a solution of 260 L water, 1.2 L NaOH (50%) and 1.4 Kg CaO for 5 minutes with slow mixing. This treatment was continued twice daily for 25 days. Following this treatment, the solution was decanted and discarded and the skins were washed with an excess of tap water for 90 minutes under constant stirring.

The skins were acidified by treatment with 14 kg HCl (35%) and 70 L water while subjecting the skins to vigorous stirring. The acid was allowed to penetrate the skins for about 6 hours. Following acidification, the skins were washed in an excess of tap water for about 4 hours or until a pH of 5.0 was reached. The pH of the skins was readjusted to 3.3–3.4 using acetic acid with a 0.5% preservative. The purified skin was then passed through a meat grinder and extruded under pressure through a series of filter sieves of constantly decreasing mesh size. The final product was a white homogeneous smooth paste of pure bovine skin-derived collagen.

In order to impart adequate pliability to the grafts in the dry state, a plasticizer such as glycerine, sorbitol or other biologically acceptable plasticizer is added to an aqueous collagen slurry before application. In a collagen slurry containing between about 0.5 to 5.0% collagen by weight, the plasticizer is present between about 4 and 12 weight percent. Between about 10 to 25 percent ethanol may be present to hasten evaporation of the water.

The most important property obtained when treating a synthetic vascular graft with a slurry of collagen and plasticizer in accordance with the invention is reduction of porosity of the porous substrate to about zero. For comparison, the porosity of twenty randomly selected uncoated Meadox Microvel synthetic vascular grafts had a mean porosity to water of 1796 ml/min-cm$^2$ at 120 mm Hg and a standard deviation of 130. After treating in accordance with the invention, the porosity is reduced to zero. The following example illustrates the method of treating the graft substrate in accordance with the invention.

EXAMPLE 2

A 50 cc syringe is filled with an aqueous slurry of 2% purified bovine skin collagen prepared in accordance with Example 1. The collagen slurry includes 8% glycerol, 17% ethanol and the remainder water and a viscosity of 30,000 cps. The syringe is placed into one end of a Meadox Medical Microvel Dacron graft 8 mm in diameter by approximately 12 cm in length. The slurry is injected into the lumen of the Microvel graft and it is massaged manually in order to cover the entire inner surface area with the collagen slurry. Any excess collagen slurry is removed through one of the open ends. The graft is permitted to dry for about ½ hour at room temperature. The coating and drying steps were repeated three more times.

Following the fourth application, the collagen was cross-linked by exposure to formaldehyde vapor for 5 minutes. The cross-linked graft was then air dried for 15 minutes and then vacuum dried for 24 hours to remove moisture and any excess formaldehyde.

EXAMPLE 3

The blood-tightness of a collagen-impregnated vascular grafts prepared in accordance with Example 2 was tested as follows. A Microvel graft 8 mm×12 cm was attached to a blood reservoir at a pressure of 120 mm Hg due to the height of the reservoir. Heprin stabilized blood was passed through the graft. Blood collected through the graft was determined and expressed in ml per min-cm$^2$. The porosity of 5 runs was determined to be 0.04, 0.0, 0.0, 0.04 and 0.03. This represents a mean porosity of 0.022 ml/min-cm$^2$ which was considered zero, as the value is within the experimental error of the study.

In order to compare this result with the blood loss for untreated Microvel, the experiment was repeated using an untreated graft fabric. The mean porosity was 36 ml/min-cm$^2$.

EXAMPLE 4

The porosity of a collagen treated fabric graft is reduced to less than about 1% after three applications as follows. A standard water porosity test used to measure water porosity of a graft is as follows. A column of water equivalent to 120 mm Hg pressure is allowed to flow through a one-half cm$^2$ orifice having a sample of graft over the orifice for one minute. The amount of water collected was measured. The milliliters of water collected per minute per cm$^2$ squared area was calculated. Several readings are taken for each sample. The porosity is reported as follows:

porosity 32 ml/min/cm$^2$.

The water porosity of a Microvel graft fabric was about 1,900 ml/min/cm$^2$. The porosity after treating was as follows:

| Number of Coatings | Porosity |
| --- | --- |
| 0 | 1,900 |
| 1 | 266 |
| 2 | 146 |
| 3 | 14 |
| 4 | 5 |
| 5 | 2 |
| 6 | 0 |

Figure 3:
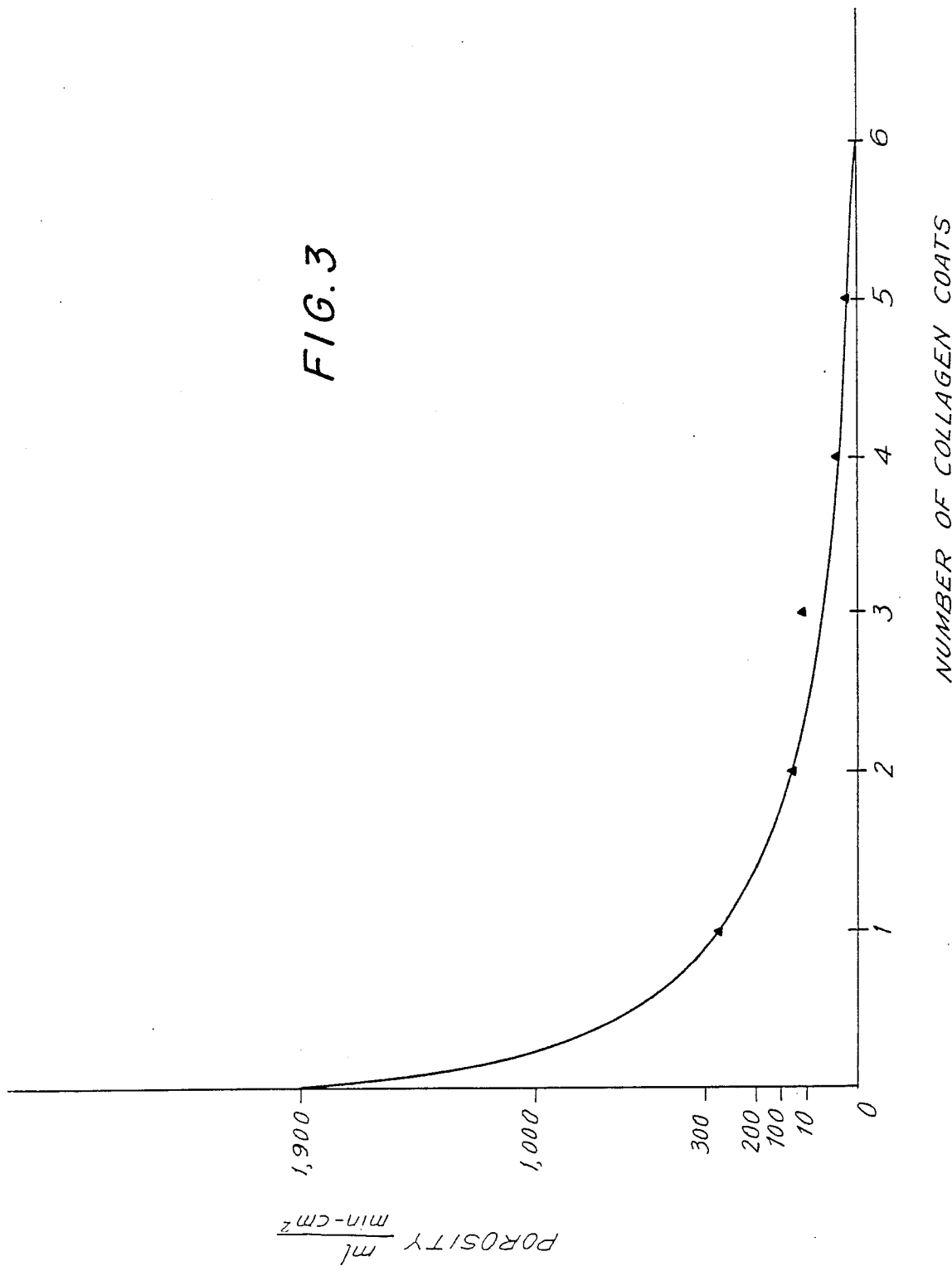
FIG. 3 is a graph showing the reduction of porosity after a series of collagen applications in accordance with the invention.

In each case the collagen coating was a bovine skin derived-plasticized slurry prepared in accordance with the composition described in Example 2. These results are set forth in the graph of FIG. 3. Based on this, it is preferable to provide a collagen impregnated graft treated with at least three applications of fibrils, and most preferably four or five with drying between each application and cross-linking after the final application to fix the collagen to the substrate.

In addition to reduced porosity, collagen treated vascular grafts in accordance with the invention exhibit reduced thrombogenicity compared to untreated grafts. The following examples demonstrate significantly less thrombogenicity of collagen impregnated vascular grafts compared to controlled.

EXAMPLE 5

Antithrombogenicity was evaluated in vitro by the method of Imai and Nose (J. Biomed, Mater Res. 6, 165, 1972). In accordance with the procedure, a volume of 0.25 ml of ACD blood (citric acid stabilized) was mixed with 25 ul of 0.1 m CaCl$_2$ and placed onto the inner surface of a collagen-impregnated Microvel graft prepared n accordance with Example 2. A similar volume was placed on an untreated Microvel graft as a control. The same geometry of the blood spot was observed after 5, 10 and 15 minutes. The clotting reaction was stopped by adding 5 ml distilled water to the test samples. Striking differences were observed between the two tested grafts and the following semi-quantitative parameters were ascertained:

|  |  | Collagen Impregnated | Plain |
| --- | --- | --- | --- |
| Rate of soaking the graft matrix with blood |  | Fast | slow |
| Thrombus formation in | 5 min | 0 | ++ |
|  | 10 min | + | +++ |
|  | 15 min | ++ | ++++ |

A comparison of thrombus formation onto the inner surface of the collagen impregnated Microvel graft and control Microvel graft was as follows. In the collagen impregnated graft there was no fibrin clot formation in 5 minutes. At 15 minutes the clot on the collagen impregnated graft was much less than in the corresponding plain grafts.

The surface of the Microvel graft in contact with the drop of blood behaved almost as hydrophobic. It took between about 10 and 15 seconds before the blood soaked into the fabric of the Dacron knitted graft. This contrasts with the collagen impregnated graft with blood soaked into the graft matrix evenly and fast.

After 5 minutes there was no thrombus residue detected on the collagen graft. At the same time, a thin but definite thrombus was present on the surface of the plain control Microvel graft. At 10 and 15 minutes, the total volume of thrombus present on the graft inner surface was less in the collagen graft than in the controls.

Based on the above observations under in vitro conditions, with no blood flow, the collagen Dacron knitted Microvel graft soaked quickly with blood, without forming any thrombus within 5 minutes. At this time the control graft showed thrombus formation. Later after 10 and 15 minutes the amount of thrombus was less in collagen impregnated grafts than in plain control Dacron grafts.

EXAMPLE 6

The thrombogenicity of collagen impregnated Microvel grafts was tested in vitro (dogs) as follows. A femoral arterial venous (AV) shunt was installed in greyhounds in deep anesthesia. A 5 centimeter long prosthetic material was adapted at both ends with plastic conical tubings for better handling. This allowed easy insertion of a test graft segment into the arterial shunt. After insertion, a venous clamp was slowly removed with the arterial end released slowly thereafter. The blood flow was circulated through the implant for 10 minutes or 30 minutes. Then, both ends of the shunt were clamped again and the inserted prosthesis removed. The excess of blood was drained off and the weight established. the presence of graft surface adhering thrombi was observed macroscopically. The grafts were then washed (three times) in excess distilled water and weighed again.

As a control a standard 6 mm diameter Dacron Microvel graft was used. This graft was pre-clotted before insertion into the shunt. Accordingly, this test provided both visual and objective gravimetric evidence of the thrombogenicity on the surface tested. The weight of blood oozing across the graft wall was also ascertained to record the difference between the tested samples.

No bleeding at all was found with collagen impregnated grafts.

After insertion of a pre-clotted control graft into the AV shunt, an average of 30 ml blood/5 cm long graft was lost in the first 5 minutes. In the next 5 minutes, only 3-5 ml blood was lost. In one of the control grafts tested for 30 minutes, minimum bleeding of 1 ml/min/5 cm through the pre-clotted graft continued for the entire test.

The collagen impregnated grafts implanted for 10 or 30 minutes showed the same pattern of resistance to thrombus formation observed macroscopically. A thin smooth layer of glistening proteinaceous material covers the collagen layer. After washing repeatedly in distilled water a continuous film of proteins (fibrin) is seen in most prosthesis. A typical clot was not observed in the sample prosthesis.

Of the five tested pre-clotted plain Dacron graft implants, three exhibited distinct multiple thrombi. These were located transverse to the direction of blood flow crossing ⅓ to ½ of the circumference. In the remaining two prosthesis, a similar skin proteinaceous layer covered the inner surface. The outer surfaces of each control graft contained large thrombi due to continuous bleeding through the wall.

Based on these observations, thrombogenicity of collagen impregnated vascular Dacron grafts was significantly less than in control pre-clotted grafts. This could be due to either reduced thrombus because of the collagen or to the thrombus formed in the control grafts due to the need for pre-clotting. As blood clotting is an event participating in excessive cell reaction with the fibrotic replacement, it is advantageous to reduce thrombus formation within the matrix of the Dacron graft leading to a lesser risk of emboli.

By applying at lesat three applications of a collagen fibril and plasticizer slurry to a synthetic porous vascular graft substrate n accordance with the invention specific desirable improvements are obtained when the graft is surgically placed in a human patient as a vascular replacement. The anticipated benefits include, but are not limited to elimination of the necessity for pre-clotting. Conventional porous grafts, although proven to be necessary for long-term patency, made it necessary for the surgeon to pre-clot the graft with the patient's blood in order to prevent excessive blood loss at the time of implant. Typically, the pre-clotting step is a time-consuming one requiring some practice and skill. Accordingly, it has been a primary objective of a collagen treatment to eliminate the need for pre-clotting synthetic grafts altogether.

The porous synthetic vascular graft substrates provide a ideal matrix for tissue ingrowth while eliminating the need for pre-clotting. Additionally, the signficantly lower thrombogenicity of collagen impregnated synthetic vascular grafts reduce the risk of emboli. Treating a synthetic vascular graft with a collagen and plasticizer slurry in a series of applications in accorance with the invention also provides a vascular graft which remains flexible with good hand.

It will thus be seen that the objects set forth above, among those made apparent from the preceding description, are efficiently attained and, since certain changes may be made in carrying out the above process and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A process for preparing a blood-tight collagen-impregnated synthetic vascular graft, comprising:
   providing a porous tubular flexible synthetic graft substrate;
   placing an aqueous slurry of water-insoluble collagen fibrils and plasticizer onto at least the inner surface of the substrate;
   massaging the substrate to insure intimate mixing of the collagen fibrils into the porous structure of the substrate;
   drying the collagen;
   cross-linking the collagen by exposure to formaldehyde vapor; and
   vacuum drying to remove excess formaldehyde.

2. A collagen fibril slurry for forming a blood-tight synthetic vascular graft comprising about 0.5 to 5.0 percent collagen fibril, 4.0 to 12.0 percent of a biologically compatible plasticizer and the balance water.

3. The slurry of claim 2, wherein the collagen fibrils are obtained by acid digestion of bovine skin.

4. The slurry of claim 2, wherein the plasticizer is selected from the group consisting of sorbitol and glycerine.

5. The process of claim 1, wherein the slurry is applied and massaged through the substrate at least three times and dried between applications.

6. A process for preparing a blood-type collagen-impregnated synthetic vascular graft, comprising:
   providing a porous tubular flexible synthetic graft substrate;
   placing a aqueous slurry of water-insoluble collagen fibrils and plasticizer onto the inner surface of the substrate;
   massaging the substrate to mature intimate mixing of the collagen fibrils into the porous structure of the substrate;
   drying the collagen;
   cross-linking the collagen by exposure to a biocompatible cross-linking agent; and
   vacuum drying to remove excess cross-linking agent.

7. The process of claim 6, wherein the substrate has a porosity of less than about 3,000 ml/min.-cm$^2$ (purified water at 120 mm Hg);

8. The process of claim 6, wherein the cross-linking agent is formaldehyde vapor.

9. The process of claim 7, wherein the cross-linking agent is formaldehyde vapor.

10. The process of claim 6, wherein the slurry is applied in at least three applications and dried between each application.

11. The process of claim 7, wherein the slurry is applied in at least three applications and dried between each application.

12. The process of claim 6, wherein the aqueous slurry contains between about 0.5 to 5.0 weight percent water-insoluble collagen fibrils.

13. The process of claim 7, wherein the aqueous slurry contains between about 0.5 to 5.0 weight percent water-insoluble collagen fibrils.

14. The process of claim 12, wherein the platicizer is present in an amount between about 4 to 12 weight percent.

15. The process of claim 13, wherein the plasticizer is present in an amount between about 4 to 12 weight percent.

* * * * *